(12) United States Patent
Banju et al.

(10) Patent No.: US 10,918,999 B2
(45) Date of Patent: Feb. 16, 2021

(54) CELL-CAPTURING FILTER, METHOD FOR MANUFACTURING CELL-CAPTURING FILTER, AND DEGRADATION DETERMINATION METHOD FOR CELL-CAPTURING FILTER

(71) Applicant: Murata Manufacturing Co., Ltd., Nagaokakyo (JP)

(72) Inventors: Masaru Banju, Nagaokakyo (JP); Wataru Yamamoto, Nagaokakyo (JP); Junko Watanabe, Nagaokakyo (JP); Takashi Kondo, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 136 days.

(21) Appl. No.: 16/176,382

(22) Filed: Oct. 31, 2018

(65) Prior Publication Data
US 2019/0060839 A1    Feb. 28, 2019

Related U.S. Application Data

(63) Continuation of application No. PCT/JP2018/010272, filed on Mar. 15, 2018.

(30) Foreign Application Priority Data

Mar. 21, 2017    (JP) .............................. JP2017-054750

(51) Int. Cl.
  *B01D 69/06*    (2006.01)
  *C12M 3/00*    (2006.01)
  *B01D 71/02*    (2006.01)
  *B01D 29/03*    (2006.01)
  (Continued)

(52) U.S. Cl.
  CPC ............. *B01D 69/06* (2013.01); *B01D 63/08* (2013.01); *B01D 67/0062* (2013.01);
  (Continued)

(58) Field of Classification Search
  None
  See application file for complete search history.

(56) References Cited

U.S. PATENT DOCUMENTS 8,273,253 B2    9/2012  Curran
8,777,017 B2    7/2014  Curran
(Continued)

FOREIGN PATENT DOCUMENTS

JP    2010520446 A    6/2010
WO    2014162810 A1    10/2014
(Continued)

OTHER PUBLICATIONS

International Search Report issued in PCT/JP2018/010272, dated Jun. 19, 2018.

*Primary Examiner* — Krishnan S Menon
*Assistant Examiner* — Brad Gordon
(74) *Attorney, Agent, or Firm* — Arent Fox LLP

(57) ABSTRACT

In a cell-capturing filter including a metal porous membrane, degradation over time is determined earlier. A cell-capturing filter includes a metal porous membrane having a plurality of through-holes that penetrate between two principal surfaces facing each other. The metal porous membrane is made of an alloy of nickel and an element selected from the group consisting of gold, platinum, and palladium, or a metal containing nickel as a main component. A metal containing copper as a main component is attached to a part of either one of the principal surfaces of the metal porous membrane. By checking a state change of the metal containing copper as a main component, degradation over time of the metal porous membrane can be determined earlier.

9 Claims, 4 Drawing Sheets

(51) Int. Cl.
*B01D 63/08* (2006.01)
*B01D 67/00* (2006.01)
*C25D 1/08* (2006.01)
*C25D 5/02* (2006.01)
*G01N 23/00* (2006.01)
*C25D 5/34* (2006.01)
*C12M 1/00* (2006.01)
*C12M 1/26* (2006.01)
*C25D 3/56* (2006.01)
*C25D 3/12* (2006.01)

(52) U.S. Cl.
CPC ........... *B01D 67/0069* (2013.01); *C12M 3/00* (2013.01); *C12M 33/14* (2013.01); *C12M 47/04* (2013.01); *C25D 1/08* (2013.01); *C25D 5/022* (2013.01); *C25D 5/34* (2013.01); *G01N 23/00* (2013.01); *B01D 29/03* (2013.01); *B01D 63/087* (2013.01); *B01D 71/022* (2013.01); *C25D 3/12* (2013.01); *C25D 3/562* (2013.01); *G01N 2223/646* (2013.01)

(56) References Cited

U.S. PATENT DOCUMENTS

| | | | |
|---|---|---|---|
| 9,291,543 B1* | 3/2016 | Robinson | G01N 17/006 |
| 10,183,083 B2 | 1/2019 | Kondo et al. | |
| 2010/0143879 A1 | 6/2010 | Curran | |
| 2013/0098827 A1 | 4/2013 | Curran | |
| 2014/0299539 A1* | 10/2014 | Takai | B01D 39/10 |
| | | | 210/506 |
| 2017/0173194 A1 | 6/2017 | Kondo et al. | |
| 2017/0269086 A1 | 9/2017 | Takai et al. | |
| 2018/0021708 A1 | 1/2018 | Takai et al. | |

FOREIGN PATENT DOCUMENTS

| | | |
|---|---|---|
| WO | 2016017755 A1 | 2/2016 |
| WO | 2016117486 A1 | 7/2016 |
| WO | 2017026348 A1 | 2/2017 |

\* cited by examiner

CELL-CAPTURING FILTER, METHOD FOR MANUFACTURING CELL-CAPTURING FILTER, AND DEGRADATION DETERMINATION METHOD FOR CELL-CAPTURING FILTER

CROSS REFERENCE TO RELATED APPLICATIONS

The present application is a continuation of International application No. PCT/JP2018/010272, filed Mar. 15, 2018, which claims priority to Japanese Patent Application No. 2017-054750, filed Mar. 21, 2017, the entire contents of each of which are incorporated herein by reference.

TECHNICAL FIELD

The present invention relates to a cell-capturing filter including a metal porous membrane in which degradation can be determined, a method for manufacturing the same, and a degradation determination method for a cell-capturing filter.

BACKGROUND OF THE INVENTION

In recent years, a filter including a metal porous membrane have been used as a cell-capturing filter that captures cells in a fluid. One example of such a filter is disclosed in Japanese Unexamined Patent Application Publication (Translation of PCT Application) No. 2010-520446.

The metal porous membrane included in such a filter becomes degraded over time, and in some cases, there is a concern that the mechanical strength of the metal porous membrane may be decreased, resulting in damage to the metal porous membrane. In such cases, the function as the filter is unlikely to be fulfilled. Furthermore, by the time that the degradation of the filter becomes apparent from its appearance, the degradation of the metal porous membrane is fairly advanced.

Accordingly, it is an object of the present invention to solve the problems of the existing techniques and provide a cell-capturing filter including a metal porous membrane in which it is possible to recognize degradation of the filter at an early stage, a method for manufacturing the same, and a degradation determination method for a cell-capturing filter.

BRIEF DESCRIPTION OF THE INVENTION

In an aspect of the present invention, a cell-capturing filter includes a metal porous membrane having a plurality of through-holes that penetrate between two principal surfaces facing each other. The metal porous membrane is made of an alloy of nickel and an element selected from the group consisting of gold, platinum, and palladium, or a metal containing nickel as a main component. A metal containing copper as a main component is attached to a part of either one of the principal surfaces of the metal porous membrane.

In another aspect of the preset invention, a method for manufacturing a cell-capturing filter including a metal porous membrane having a plurality of through-holes includes a step of forming a metal film containing copper as a main component on a surface of a substrate; a step of forming a resist film on a surface of the metal film; a step of exposing the resist film, thereby forming a resist image having a plurality of groove portions for partially exposing the metal film; a step of performing a plating process, by using the metal film as a feeding electrode, to deposit an alloy of nickel and an element selected from the group consisting of gold, platinum, and palladium, or a metal containing nickel as a main component within the groove portions, thereby forming a metal porous membrane; a step of removing the resist image: and a step of removing the substrate and the metal film. In the step of removing the substrate and the metal film, the metal containing copper as a main component that constitutes the metal film is left on a surface of the metal porous membrane.

In another aspect of the preset invention, a degradation determination method that determines the degree of degradation of a cell-capturing filter including a metal porous membrane includes a step of preparing a cell-capturing filter in which a metal containing copper as a main component is attached to a part of either one of principal surfaces of the metal porous membrane made of an alloy of nickel and an element selected from the group consisting of gold, platinum, and palladium, or a metal containing nickel as a main component; and a step of determining the degree of degradation of the metal porous membrane on the basis of a state change of the metal containing copper as a main component that is attached to the metal porous membrane.

According to the present invention, it is possible to provide a cell-capturing filter including a metal porous membrane in which degradation over time can be determined earlier, a method for manufacturing the same, and a degradation determination method for a cell-capturing filter.

DETAILED DESCRIPTION OF THE PREFERRED EMBODIMENTS

Figure 1:
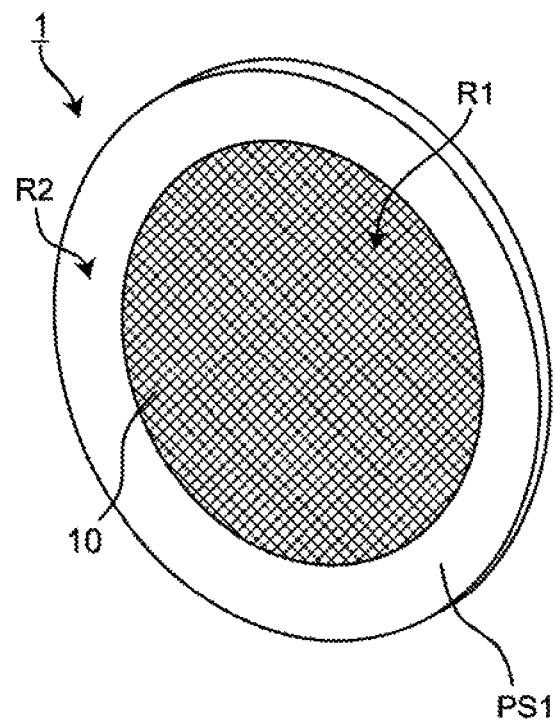
FIG. 1 is a schematic diagram of a cell-capturing filter according to an embodiment of the present invention.

In an aspect of the present invention, a cell-capturing filter includes a metal porous membrane having a plurality of through-holes that penetrate between two opposed principal surfaces. The metal porous membrane is made of an alloy of nickel and an element selected from the group consisting of gold, platinum, and palladium, or a metal containing nickel as a main component. A metal containing copper as a main component is attached to a part of either one of the principal surfaces of the metal porous membrane.

With this configuration, it is possible to determine the degradation of the cell-capturing filter, including the metal porous membrane, over time by checking a state change of the metal containing copper as a main component.

The metal porous membrane may include a central region where the plurality of through-holes are arranged and a peripheral region which surrounds the central region, and the metal may be attached to the peripheral region.

In such a configuration, the degradation over time of the cell-capturing filter can be determined by using the metal disposed in the peripheral region, without affecting the central region which has the function as a cell-capturing filter.

In another aspect of the present invention, a group of cell-capturing filters of the same lot, each of which includes a metal porous membrane having a plurality of through-holes that penetrate between two opposed principal surfaces, may include at least one cell-capturing filter having any of the configurations described above.

Since cell-capturing filters of the same lot are manufactured at the same time, it is assumed that the cell-capturing filters degrade over time in the same manner. Therefore, when a group of cell-capturing filters from the same lot includes at least one cell-capturing filter having the metal attached thereto, it is possible to determine the degradation over time of the group of cell-capturing filters of the same lot.

In another aspect of the preset invention, a method for manufacturing a cell-capturing filter including a metal porous membrane having a plurality of through-holes includes a step of forming a metal film containing copper as a main component on a surface of a substrate; a step of forming a resist film on a surface of the metal film; a step of exposing the resist film, thereby forming a resist image having a plurality of groove portions for partially exposing the metal film; a step of performing a plating process, by using the metal film as a feeding electrode, to deposit an alloy of nickel and an element selected from the group consisting of gold, platinum, and palladium, or a metal containing nickel as a main component within the groove portions, thereby forming a metal porous membrane; a step of removing the resist image; and a step of removing the substrate and the metal film. In the step of removing the substrate and the metal film, the metal containing copper as a main component that constitutes the metal film is left on a surface of the metal porous membrane.

According to such a configuration, in the method of manufacturing a filter including a metal porous membrane, the metal film, which is used as a feeding electrode in the plating process for forming the metal porous membrane, is not entirely removed, but is partially left. Thereby, without adding a step of placing the metal containing copper as a main component, in which, in an environment of capturing cells, the state change is likely to proceed rapidly compared with the metal containing nickel as a main component or an alloy of nickel and an element selected from the group consisting of gold, platinum, palladium that mainly constitutes the metal porous membrane, on the surface of the metal porous membrane, the metal containing copper as a main component can be disposed in the step of removing the metal film. Accordingly, it is possible to provide a method for manufacturing a cell-capturing filter including a metal porous membrane in which degradation over time can be determined earlier.

In another aspect of the preset invention, a degradation determination method that determines the degree of degradation of a cell-capturing filter including a metal porous membrane includes a step of preparing a cell-capturing filter in which a metal containing copper as a main component is attached to a part of either one of principal surfaces of the metal porous membrane made of an alloy of nickel and an element selected from the group consisting of gold, platinum, and palladium, or a metal containing nickel as a main component; and a step of determining the degree of degradation of the metal porous membrane on the basis of a state change of the metal containing copper as a main component that is attached to the metal porous membrane.

According to such a configuration, by checking a state change of the metal containing copper as a main component, degradation over time of the cell-capturing filter including the metal porous membrane can be determined earlier.

Embodiments of the present invention will be described below with reference to the attached drawings. Furthermore, in the drawings, in order to facilitate explanation, the elements are indicated in an exaggerated form.

Embodiment 1

(Overall Structure of Filter)

Figure 2:
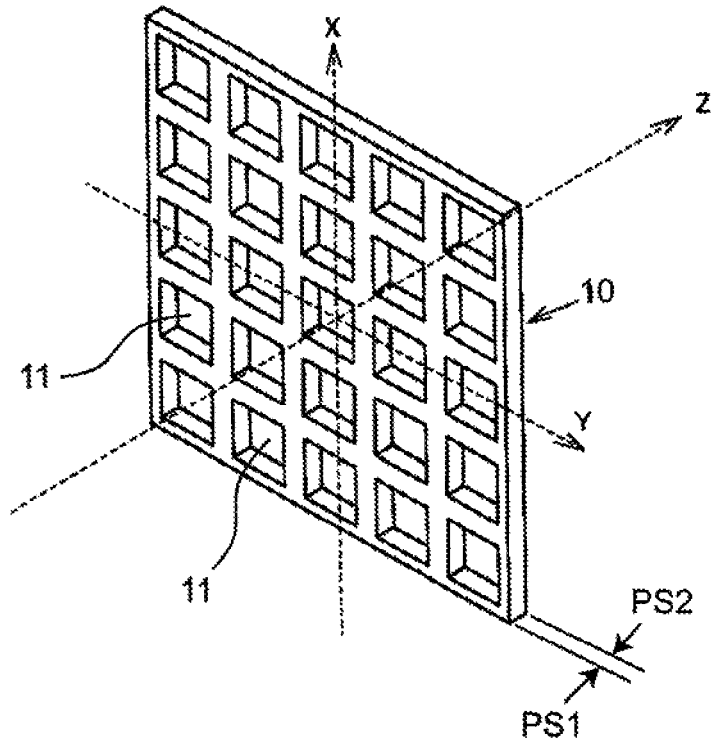
FIG. 2 is a partially enlarged view of a metal porous membrane in the filter shown in FIG. 1.

FIG. 1 is a schematic diagram of a cell-capturing filter 1 (hereinafter, referred to as the "filter 1") according to Embodiment 1 of the present invention. FIG. 2 is a partially enlarged view of the filter 1. In FIG. 2, the X and Y directions extend along the surface of the filter 1 and are orthogonal to each other, and the Z direction is a thickness direction of the filter 1 and is orthogonal to the X direction and the Y direction.

As shown in FIG. 1, the filter 1 includes a metal porous membrane 10 having a plurality of through-holes 11 that extend in the thickness direction of the porous membrane and which extend through the opposed surfaces of the porous membrane. The metal porous membrane 10 includes a central region R1 where the plurality of through-holes 11 are arranged and a peripheral region R2 which surrounds the central region R1. In Embodiment 1, the central region R1 is a circular region, and the peripheral region R2 is an annular region. The peripheral region R2 does not have any through-holes 11 formed therein. Furthermore, in the filter 1, a frame body may be provided so as to sandwich and hold the peripheral region R2 of the metal porous membrane 10 so that the handling ability of the filter 1 can be enhanced.

The metal porous membrane 10 allows a fluid containing a filtration object (or capture object) to pass through the through-holes 11 and thereby isolates the filtration object from the fluid. In the present description, the term "filtration object" means an object to be filtered by the metal porous membrane 10. Examples of the filtration object include a biological substance and PM2.5. The term "biological substance" means a substance derived from an organism, such as a cell (eukaryote), bacteria (eubacteria), or a virus. Examples of the cell (eukaryote) include induced pluripotent stem cells (iPS cells), ES cells, stem cells, mesenchymal stem cells, mononuclear cells, single cells, cell masses, floating cells, adherent cells, nerve cells, white blood cells, cells for regenerative medicine, self cells, cancer cells, circulating tumor cells (CTCs), HL-60, HELA, and fungi. Examples of the bacteria (eubacteria) include colon bacilli and tubercle bacilli.

As shown in FIG. 1, the metal porous membrane 10 includes a circular metal mesh. Furthermore, as shown in FIG. 2, the metal porous membrane 10 is a structure having first and second principal surfaces PS1 and PS2 which face (oppose) one another and a plurality of through-holes 11 that extend between the first and second principal surfaces PS1 and PS2 and penetrate the two surfaces. The plurality of through-holes 11 are preferably arranged periodically, in the central region R1 of the metal porous membrane 10 as viewed from the first and second principal surfaces PS1 and PS2. The metal porous membrane 10 is preferably mainly composed of nickel and has, for example, a diameter of 6 mm and a thickness of 1.2 μm.

As shown in FIG. 2, the metal porous membrane 10 is a plate-shaped structure (lattice-like structure) in which a plurality of through-holes 11 are arranged, in a matrix, at certain intervals. In this embodiment, the through-holes 11 each have a square shape when viewed from the first principal surface PS1 side of the metal porous membrane 10, i.e., when viewed in the Z direction (see the coordinate system of FIG. 2). The through-holes 11 are provided at equal intervals in two arrangement directions parallel to sides of the square, i.e., in the X and Y directions shown in FIG. 2. The shape of the through-hole 11 is not limited to square, but may be, for example, rectangular, circular, elliptical, or the like. Furthermore, the arrangement of holes is not limited to the square lattice arrangement. For example, in a tetragonal arrangement, a rectangular arrangement in which intervals in two arrangement directions are not equal may be used. Furthermore, a triangular lattice arrangement, quasi-periodic arrangement, or the like may be used.

The shape and size of the through-hole 11 are appropriately designed depending on the size and shape of the filtration object to be filtered. In Embodiment 1, the through-hole 11 is, for example, designed so as to have a square shape, when viewed from the first principal surface PS1 side of the metal porous membrane 10, i.e., when viewed in the Z direction, with a length of 0.1 to 500 µm and a width of 0.1 to 500 µm. The distance between the adjacent two through-holes 11 is, for example, larger than one times the size of the through-hole 11 and equal to or smaller than ten times the size of the through-hole 11, and more preferably equal to or smaller than three times the size of the through-hole 11. Alternatively, the aperture ratio is preferably 10% or more.

Figure 3:
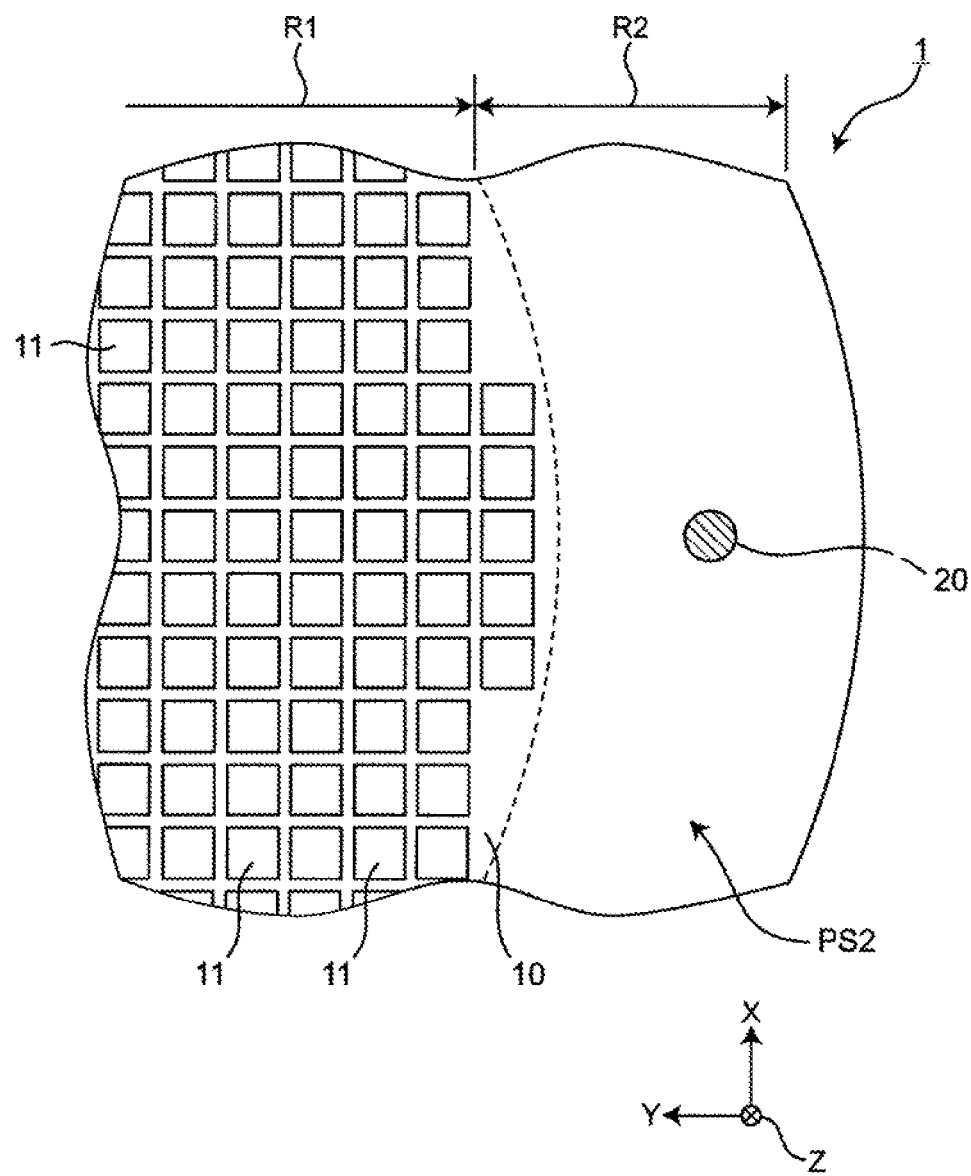
FIG. 3 is a partially enlarged view of the metal porous membrane in the filter shown in FIG. 1, viewed from the second principal surface side.

FIG. 3 is a partially enlarged view showing the boundary between the central region R1 and the peripheral region R2 and the vicinity thereof, viewed from the second principal surface PS2 side of the metal porous membrane 10.

As shown in FIG. 3, an indicator 20 is disposed in the peripheral region R2 on the second principal surface PS2 of the metal porous membrane 10. The metal constituting the indicator 20 is preferably a metal in which, in an environment of capturing cells, the state change proceeds rapidly compared with the main material of the metal porous membrane 10, that is, the state of the metal constituting the indicator 20 changes more quickly than the state of the main material of the porous membrane 10. In Embodiment 1, nickel is preferably used as the main material of the metal porous membrane 10, and copper is preferably used as the material of the indicator 20. When the degradation over time of the metal porous membrane 10 proceeds, the state change of copper constituting the indicator 20 proceeds more rapidly than that of nickel which is the main material of the metal porous membrane 10.

When the main material of the metal porous membrane 10 has nickel as its primary component, a dense oxide layer will be formed on the outside of the metal porous membrane. That oxide layer will protect the inside of the metal porous membrane 10 with the result that oxidation is unlikely to proceed into the inside of the metal layer, and the oxide layer is maintained thin. Therefore, the metallic luster of the metal layer is maintained, and a change of color of the metal layer with aging is unlikely to occur. On the other hand, when the metal indicator 20 is made of a metal layer containing copper as its main component, porous oxides (CuO, Cu2O) are formed on the surface of copper and oxidation is likely to proceed into the inside of a metal layer containing copper as a main component. Therefore, the thickness of the oxide layer increases with aging, and the color tone of the oxides strongly appears in the metal layer. That is, a change of color with aging is likely to occur in copper compared with nickel. From such a viewpoint, preferably, the metal porous membrane 10 is made of a metal containing nickel as a main component, and the indicator 20 is made of a metal containing copper as a main component.

As used herein, a metal containing nickel as a main component refers to a metal in which the percentage of nickel (mass ratio) is the highest of the components contained in the metal. As used herein, a metal containing copper as a main component refers to a metal in which the percentage of copper (mass ratio) is the highest of the components contained in the metal.

Embodiment 1 shows an example in which the metal porous membrane 10 is made of a metal containing nickel as a main component. However, a metal porous membrane may be made of an alloy of nickel and one or more elements selected from the group consisting of gold, platinum, and palladium. As such an alloy, for example, an alloy of palladium (80 wt %) and nickel (20 wt %), an alloy of gold (95 wt %) and nickel (5 wt %), or an alloy of platinum (90 wt %) and nickel (10 wt %) may be used. The composition ratios of these metals may be measured, for example, by using an ICP-AES (inductively coupled plasma-atomic emission spectrometer).

In the preferred embodiment, the indicator 20 is disposed on a part of either one of the first and second principal surfaces PS1 and PS2 of the metal porous membrane 10. However, the indicator 20 may be disposed in the central region R1, or in both the central region R1 and the peripheral region R2, on either one of the principal surfaces. Furthermore, while a single indicator 20 is shown in the drawings, a plurality of indicators 20 may be disposed at a plurality of spaced positions on the filter 1 (e.g., at a plurality of spaced position on the peripheral region R2).

The size of the indicator 20 is determined by the manner in which the state of change is detected. For example, when the state change (typically the oxidation state) is checked visually, the indicator 20 preferably has a visually recognizable size. On the other hand, when the oxidation state of the indicator 20 is checked on the basis of the result of analysis with an analyzer, such as an X-ray analyzer, the indicator 20 is preferably of a size that can be analyzed with the analyzer even though the indicator 20 cannot be visually recognized. In Embodiment 1, the indicator 20 is preferably formed with a diameter of about 3 µm when viewed in a direction orthogonal to the second principal surface PS2. In order for the indicator 20 to be easily visually checked, it is preferably disposed at least on the peripheral region R2.

(Degradation Determination Method for Filter)

Figure 4:
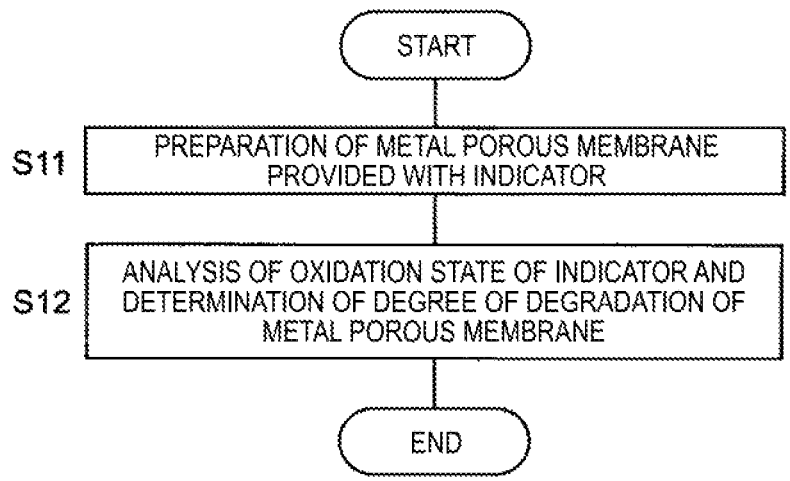
FIG. 4 is a flowchart of a degradation determination method for a filter according to an embodiment of the present invention.

An example of a method of determining the degradation over time of the metal porous membrane 10 in the cell-capturing filter 1 according to Embodiment 1 will be described below. FIG. 4 shows a flowchart of a degradation determination method for the filter 1.

In step S11, a filter 1 including a metal porous membrane 10 on which an indicator 20 is disposed, is prepared (or obtained). The filter 1 on which the indicator 20 is disposed may be prepared by attaching a metal, which, in an environment of capturing cells, changes state more rapidly than the change of state of the main material of the metal porous membrane 10. Furthermore, the filter 1 may be prepared by producing the filter 1 on which the indicator 20 is disposed by a manufacturing method which will be described later.

In step S12, a state change of the indicator 20 is analyzed, and the degree of degradation of the metal porous membrane 10 is determined on the basis of the analysis result. For example, by using an X-ray analyzer, an oxidation state, as the state change of the indicator 20, is analyzed. By comparing the analysis result with a threshold value of the oxidation state, the degree of degradation of the metal porous membrane 10 can be determined. The degree of degradation may be determined by using only one threshold value, or the degree of degradation (rate of degradation) may be determined in multiple stages by using a plurality of threshold values.

In the case where it is determined that the metal porous membrane 10 has degraded over time, the currently used filter 1 is replaced with a new filter 1.

In the example of the degradation determination method described above, the state change (e.g., oxidation state) of the indicator 20 is preferably analyzed using X-rays. However, the state change may be checked without using X-rays. For example, the state change of the indicator 20 may be visually checked (e.g., the degree of change of color due to oxidation may be visually checked). For example, by checking a change of volume due to oxidation of the indicator 20, the state change may be checked. When oxidation of the indicator 20 proceeds, the volume of the indicator 20 tends to increase. For example, the state change of the indicator 20 may be checked on the basis of light scattering. As the indicator 20 oxidizes, the smoothness of the surface of the indicator 20 is lost, and irregularities are formed on the surface. As a result, higher-order light scattering tends to intensify.

(Method for Manufacturing Filter)

Figure 5:
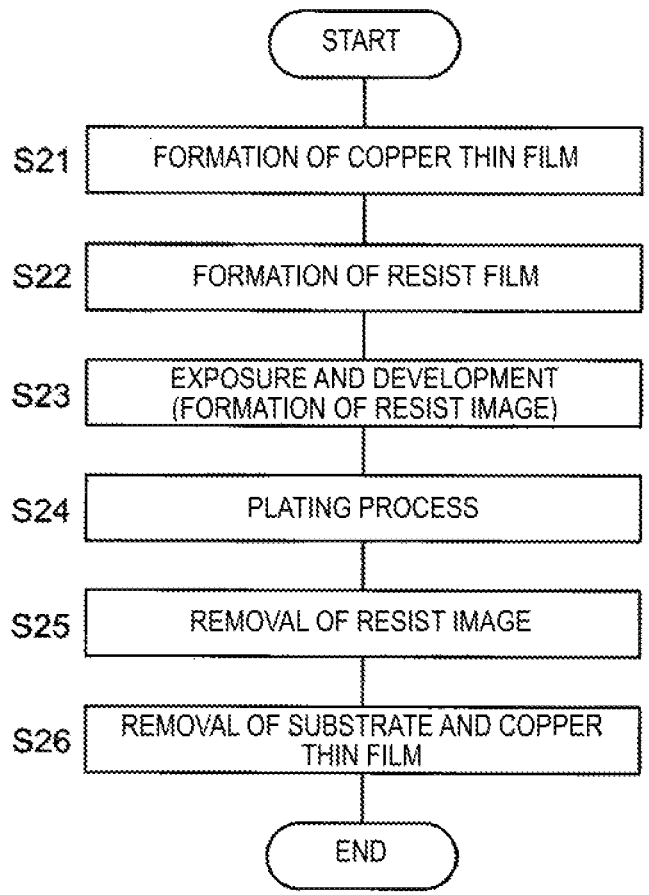
FIG. 5 is a flowchart of a method for manufacturing a filter according to an embodiment of the present invention.

Next, an example of a method for manufacturing a cell-capturing filter 1 according to Embodiment 1 will be described. FIG. 5 shows a flowchart of the method for manufacturing the filter 1, and FIGS. 6(A) to 6(F) are partial cross-sectional views (partial cross-sectional views of the boundary between the central region R1 and the peripheral region R2 and the vicinity thereof) showing the steps in the method of manufacturing the filter 1.

Figure 6:
FIGS. 6(A)-6(F) shows schematic cross-sectional views illustrating the steps in the method for manufacturing a filter shown in FIG. 5.
Figure 6:
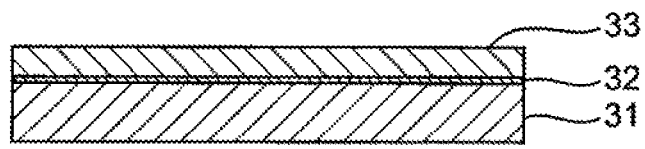
Figure 6:
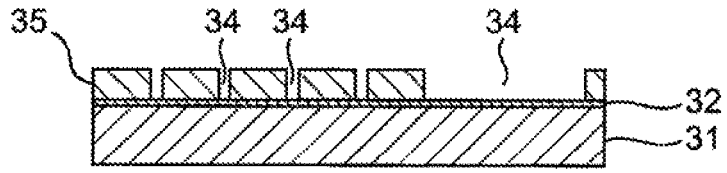
Figure 6:
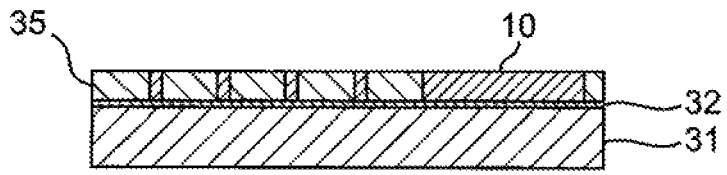
Figure 6:
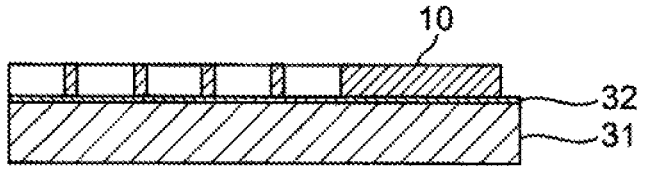
Figure 6:
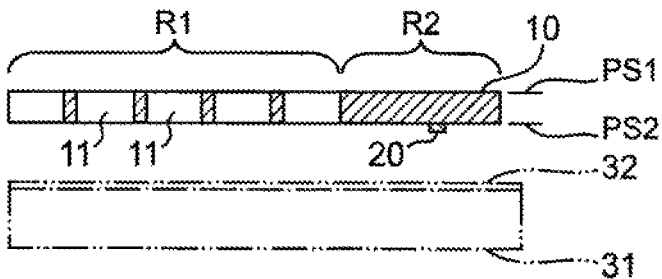

As shown in FIG. 5, a copper thin feeding film is formed in step S21. As shown in FIG. 6(A), a metal film made of a first metal is formed on a substrate 31 made of silicon or the like. The first metal is a metal whose state, in an environment of capturing cells, changes rapidly compared with the main material constituting the metal porous membrane 10. For example, the first metal may be a metal containing copper as a main component and a copper thin film 32 is formed on the substrate 31. The copper thin film 32 can be formed, for example, by vapor deposition or sputtering. Formation by sputtering can provide good surface quality of the film compared with formation by vapor deposition. The copper thin film 32 is used as a feeding electrode in a plating process described below.

Next, as shown in FIG. 6(B), a resist film 33 is formed on the copper thin film 32 (step S22: formation of resist film). Specifically, a resist is applied, for example, by spin-coating onto the copper thin film 32, followed by a drying treatment, thereby to form the resist film 33. The resist film 33 is formed, for example, with a thickness of about 2 μm.

Next, as shown in FIG. 6(C), the resist film 33 is exposed and developed to form a resist image 35 having groove portions 34, which are obtained by removing portions corresponding to the metal porous membrane 10 from the resist film 33 (step S23: exposure and development (formation of resist image). The copper thin film 32 is exposed (partially exposed) at the bottoms of the groove portions 34.

Next, as shown in FIG. 6(D), in the resist image 35, a second metal containing nickel as a main component is deposited within the groove portions 34 to form a metal porous membrane 10 within the groove portions 34 (step S24: plating process). The metal porous membrane 10 is formed, for example, by performing electrolytic plating, using the copper thin film 32 as a feeding electrode.

Next, as shown in FIG. 6(E), by performing immersion in a solvent (e.g., acetone), the resist image 35 is dissolved and separated from the copper thin film 32 (step S25: removal of resist image).

Subsequently, as shown in FIG. 6(F), the copper thin film 32 and the substrate 31 are removed (step S26: removal of substrate and copper thin film). Specifically, by removing the copper thin film 32 by etching using an etchant, the substrate 31 is separated from the metal porous membrane 10. At this time, the copper thin film 32 is not entirely removed, but etching is performed on the copper thin film 32 such that the copper thin film 32 is partially left attached to the principal surface of the metal porous membrane 10. A portion of the copper thin film 32 remaining on the principal surface of the metal porous membrane 10 in such a manner serves as an indicator 20. The indicator 20 is attached to the peripheral region R2 on the second principal surface PS2 of the metal porous membrane 10. By adjusting one or more parameters selected from the group consisting of the thickness of the copper thin film 32, the composition of the etchant, and the etching time, etching can be achieved such that the copper thin film 32 is partially left.

Through the procedure described above, the filter 1 in which the indicator 20 is disposed on the second principal surface PS2 of the metal porous membrane 10 is produced. The manufacturing method described with reference to FIG. 5 and FIGS. 6(A) to 6(F) is merely an example, and other manufacturing methods may be used. For example, in step S26, the copper thin film 32 may be completely removed, and then a step of forming an indicator 20 on the principal surface of the metal porous membrane may be provided.

In Embodiment 1, the indicator 20 is made of a metal whose state, in an environment of capturing cells, is more likely to change than the main material of the metal porous membrane 10 and is preferably attached to either one of the principal surfaces of the metal porous membrane 10. Thereby, by checking the state of the indicator 20, degradation over time of the metal porous membrane 10 can be determined. Accordingly, degradation over time of the filter 1 including the metal porous membrane 10 can be determined earlier.

Furthermore, the indicator 20 is preferably disposed not in the central region R1 where a plurality of through-holes 11 are arranged, but in the peripheral region R2. In such a configuration, without affecting the filtration treatment and the like in the central region R1 which has the function as a filter, degradation over time of the filter 1 can be determined by using the indicator 20 disposed in the peripheral region R2.

Furthermore, since filters 1 of the same lot are manufactured at the same time, it is assumed that the filters 1 degrade over time in the same manner. For example, when a group of filters from the same lot includes at least one filter 1 having the indicator 20 attached thereto, it is possible to determine the degradation over time of the group of filters of the same lot.

Furthermore, in the process of manufacturing the filter 1, in the step of removing the copper thin film 32, which is used as a feeding electrode during plating for forming the metal porous membrane 10, from the metal porous membrane 10, the copper thin film 32 is not entirely removed, but is partially left and used as the indicator 20. Thereby, without adding a separate step of placing copper, in which the state of change is more likely to occur compared with the main material of the metal porous membrane 10, on the principal surface of the metal porous membrane 10, the copper indicator 20 may be formed by simply removing less than all of the copper used as the feeding electrode. Accordingly, it is possible to provide a method for manufacturing a filter 1 including a metal porous membrane 10 in which degradation over time can be determined earlier, as a more efficient manufacturing method.

An example of a method for manufacturing a cell-capturing filter according to the present invention will be described below.

EXAMPLE

In this example, by using a metal containing copper as a main component as a first metal and using nickel as a second metal, a filter 1 was produced in which an indicator 20 made of the first metal was attached to a part of one of principal surfaces of a metal porous membrane 10 mainly composed of the second metal. Specifically, by carrying out steps S21 to S26 shown in FIG. 5, the filter 1 was produced. As the first metal, a metal having a copper content of 99 wt % was used, and as the second metal, a metal having a nickel content of 99 wt % was used. The composition ratios of these metals are values measured by using an ICP-AES (inductively coupled plasma-atomic emission spectrometer).

First, in step S21, a copper thin film was formed on an upper surface of a substrate made of silicon by using a sputtering system. The copper thin film was formed, by using argon gas as a sputtering gas, in the sputtering system with a degree of vacuum of 5.0×10-4 Pa and an applied DC power of 500 W. The sputtering time was set to 120 minutes, and a copper thin film with a film thickness of 2 μm was formed.

Next, in step 22, a resist film with a predetermined film thickness was formed on the copper thin film using a spin coater. Specifically, after a resist material was applied onto the copper thin film, a solvent was volatilized at 130° C. in a nitrogen atmosphere, followed by cooling, and thereby, a resist film was formed. A novolac resin and an organic solvent were used as the resist material, and a resist film with a film thickness of 2 μm was formed at a number of revolutions of the spin coater of 1,130 rpm.

Next, in step S23, the resist film was exposed and developed to form groove portions corresponding to a metal porous membrane in the resist film, and thereby, a resist image was obtained. The exposure was performed by irradiating the resist film with light including a wavelength of 365 nm with an energy density of 2,500 J/m2 for 0.25 seconds. Then, the portions of the resist film exposed to light were brought into contact with an alkaline solution and removed, thereby to form groove portions.

Next, in step S24, by using electrolytic plating in which the previously formed copper thin film was used as a feeding electrode, a metal porous membrane made of a plating film mainly composed of a nickel material was formed within the groove portions of the resist image. First, as a pretreatment, the substrate provided with the copper thin film and the resist image was immersed in dilute sulfuric acid for 60 seconds so as to activate the surface of the copper thin film exposed at the bottoms of the groove portions of the resist image. Then, while vibrating the substrate in a nickel sulfamate plating solution (liquid temperature 55° C., pH 4.0), electrolytic plating was performed, using the copper thin film as a feeding electrode. The plating rate was 0.5 μm/min.

Next, in step S25, by performing immersion in a solvent, the resist image was dissolved and separated from the copper thin film. An acetone solution was used as the solvent, and by applying ultrasonic waves for 15 minutes in the acetone solution, dissolution and separation of the resist image were accelerated.

Next, in step S26, the copper thin film and the substrate were removed. Specifically, by using a mixed solution of acetic acid, aqueous hydrogen peroxide, and pure water with a volume ratio of 10:10:20 as an etchant, etching was performed on the copper thin film for an etching time of 24 hours. Thereby, the copper thin film and the substrate were removed, and a cell-capturing filter including a metal porous membrane according to Example was completed.

Comparative Example

A method for manufacturing a cell-capturing filter according to Comparative Example will now be described.

In Comparative Example, steps S21 and S26 are different from those of Example described above. Therefore, the points of difference only will be described.

First, a copper thin film was formed on an upper surface of a substrate made of silicon by using a sputtering system. The copper thin film was formed, by using argon gas as a sputtering gas, in the sputtering system with a degree of vacuum of 5.0×10-4 Pa and an applied DC power of 500 W. The sputtering time was set to 30 minutes, which was shorter than that of Example, and a copper thin film with a film thickness of 0.5 μm, which was smaller than that of Example, was formed.

Subsequently, after performing formation of a resist film, exposure and development, a plating process, and removal of a resist image, the copper thin film and the substrate were removed. Specifically, by using a mixed solution of acetic acid, aqueous hydrogen peroxide, and pure water with a volume ratio of 1:1:20 as an etchant, etching was performed on the copper thin film for an etching time of 48 hours. Thereby, the copper thin film and the substrate were removed, and a cell-capturing filter including a metal porous membrane according to Comparative Example was completed.

Upon checking the metal porous membrane of the cell-capturing filter of Example, it was confirmed that a part of the copper thin film remained as an indicator on the principal surface provided with the copper thin film. On the other hand, in the metal porous membrane of the cell-capturing filter of Comparative Example, the remainder of the copper thin film corresponding to an indicator was not confirmed. Furthermore, in order to allow a part of the copper thin film to remain as an indicator, for example, preferably, the film thickness of the copper thin film is increased and etching is performed for a short time using an etchant having an adjusted composition.

Furthermore, by appropriately combining any two or more of the various embodiments described above, their respective effects can be exhibited.

INDUSTRIAL APPLICABILITY

According to the present invention, a metal, in which, in an environment of capturing cells, the state change is likely to proceed rapidly compared with the material constituting a metal porous membrane, is attached to a part of either one of the principal surfaces of the metal porous membrane included in a cell-capturing filter, and by checking the state change of the metal, degradation over time of the metal porous membrane can be determined. Accordingly, the present invention can be usefully applied to various technical fields in which such a cell-capturing filter is used, for example, the fields of chemical analysis, drug development and manufacturing, clinical laboratory examination, public health management, environmental measurement, and the like.

REFERENCE SIGNS LIST 1 filter
10 metal porous membrane
11 through-hole
20 indicator
PS1 first principal surface
PS2 second principal surface
R1 central region
R2 peripheral region

The invention claimed is:
1. A cell-capturing filter comprising:
(a) a metal porous membrane having a plurality of through-holes that extend through the membrane and penetrate two opposed principal surfaces of the membrane, the metal porous membrane being made of:
(i) an alloy of nickel and an element selected from the group consisting of gold, platinum, and palladium; or
(ii) a metal containing nickel as a main component; and
(b) a metal indicator which is attached to only a part of one or both of the principal surfaces of the metal porous membrane, the metal indicator containing copper as a main component,
wherein the metal constituting the indicator is configured to change its state more quickly than that of the metal of the metal porous membrane, the change in state being a change in oxidation state, color, or volume.

2. The cell-capturing filter according to claim 1, wherein:
the metal porous membrane includes a central region where the plurality of through-holes are arranged and a peripheral region which surrounds the central region and does not include the through holes; and
the metal indicator is attached to the peripheral region but not the central region.

3. A group of cell-capturing filters of the same lot, each of the cell-capturing filters comprising:
a metal porous membrane having a plurality of through-holes that extend through the membrane and penetrate two opposed principal surfaces of the membrane and at least one of the cell-capturing filters having the structure of the cell capturing filter of claim 1.

4. The group of cell-capturing filters according to claim 3, wherein the metal porous membrane of the at least one of the cell capturing filters includes:
a central region where the plurality of through-holes are arranged;
a peripheral region which surrounds the central region and does not contain the through-holes; and
the metal indicator being attached to the peripheral region but not to the central region.

5. A degradation determination method for determining the degree of degradation of the filter of claim 1, the method comprising
determining the degree of degradation of an outer surface of the metal porous membrane on the basis of a state change of the metal indicator.

6. The cell-capturing filter according to claim 1, wherein the metal indicator is attached to only one of the principle surfaces of the metal porous membrane.

7. A cell-capturing filter comprising:
(a) a metal porous membrane having a plurality of through-holes that extend through the membrane and penetrate two opposed principal surfaces of the membrane, the metal porous membrane being made of:
(i) an alloy of nickel and an element selected from the group consisting of gold, platinum, and palladium; or
(ii) a metal containing nickel as a main component; and
(b) a plurality of metal indicators containing copper as a main component, each of the metal indicators being attached to only a part of a respective one of the principal surfaces of the metal porous membrane,
wherein the metal constituting each of the metal indicators is configured to change its state more quickly than that of the metal of the metal porous membrane, the change in state being a change in oxidation state, color, or volume.

8. The cell-capturing filter according to claim 7, wherein:
the metal porous membrane includes a central region where the plurality of through-holes are arranged and a peripheral region which surrounds the central region and does not contain the through-holes; and
the plurality of metal indicators are attached to only the peripheral region of the metal porous membrane.

9. The cell-capturing filter according to claim 7, wherein all of the metal indicators are attached to only one of the principle surfaces of the metal porous membrane.

* * * * *